(12) United States Patent
Thomas et al.

(10) Patent No.: US 7,552,814 B1
(45) Date of Patent: Jun. 30, 2009

(54) OBJECT TO BE INSPECTED INCLUDING SMALL DIAMETER BOTTLE

(75) Inventors: Alan E. Thomas, Clearwater, FL (US); Richard B. Otto, Crystal Beach, FL (US)

(73) Assignee: Emhart Glass S.A. (CH)

( * ) Notice: Subject to any disclaimer, the term of this patent is extended or adjusted under 35 U.S.C. 154(b) by 0 days.

(21) Appl. No.: 11/999,842

(22) Filed: Dec. 7, 2007

(51) Int. Cl.
B65G 37/00 (2006.01)

(52) U.S. Cl. .................. 198/346.1; 198/456; 198/472.1; 198/502.2

(58) Field of Classification Search .............. 198/346.1, 198/456, 472.1, 502.2, 690.1, 803.6
See application file for complete search history.

(56) References Cited

U.S. PATENT DOCUMENTS

| | | | |
|---|---|---|---|
| 5,388,707 A * | 2/1995 | Stivison et al. .............. 209/602 |
| 5,762,174 A * | 6/1998 | Risley et al. ................ 198/456 |
| 5,979,635 A * | 11/1999 | Calhoun ..................... 198/456 |
| 6,061,125 A * | 5/2000 | Thomas et al. ........... 356/237.1 |
| 6,374,987 B1 * | 4/2002 | Heuft et al. ................. 198/416 |
| 6,755,298 B1 * | 6/2004 | Heuft et al. ............. 198/370.07 |
| 6,822,181 B2 * | 11/2004 | Linton ......................... 209/524 |
| 7,342,376 B2 * | 3/2008 | Raupp ........................ 318/600 |

* cited by examiner

*Primary Examiner*—Douglas A Hess
(74) *Attorney, Agent, or Firm*—Reinhart Boerner Van Dueren S.C.

(57) ABSTRACT

A machine for inspecting a container having a vertical axis has an inspection station including an inspection device for carrying out an inspection on a transparent container relative to a vertical inspection axis. The bottle is delivered to the inspection station by a conveyor, which includes structure for engaging the sidewall of the bottle. The invention is an object to be inspected by such an inspection machine, which includes a container like adaptor having a vertical axis, and configured for handling by the conveyor structure so that when the container like adaptor engages the structure, the conveyor will deliver the container like adaptor to the inspection station. The container like adaptor has a horizontal top surface and a vertical axis, and a magnet is mounted in the top surface having a centering axis coincident with the vertical axis of the container like adaptor. The object to be inspected additionally includes a transparent bottle located on top of the magnet having metallic material in the bottom portion thereof so that the magnet will operate on the metallic material to locate the axis of the transparent bottle coincident with the centering axis of the magnet.

7 Claims, 2 Drawing Sheets

OBJECT TO BE INSPECTED INCLUDING SMALL DIAMETER BOTTLE

The present invention relates to machines which inspect bottles (containers) for defects.

BACKGROUND OF THE INVENTION

Transparent containers are conventionally engaged at an inspection location to locate the axis of the container coincident with the axis of the inspection operation. With larger containers, there will always be areas of the container that are not engaged so that inspection of these exposed areas is possible. In certain situations, however, a container can be so small that any engagement of the outer wall effectively prevents inspection.

OBJECT OF THE INVENTION

It is accordingly an object of the present invention to present a container at an inspection station with the axis of the container at the desired location and with the container stable for inspection so that unobstructed viewing of the container profile is possible for non-contact inspection (inspection, measurement, etc,).

Other objects and advantages of the present invention will become apparent from the following portion of this specification and from the accompanying drawings, which illustrate, in accordance with the mandate of the patent statutes, a presently preferred embodiment incorporating the principles of the invention.

BRIEF DESCRIPTION OF THE PREFERRED EMBODIMENT

Figure 1:
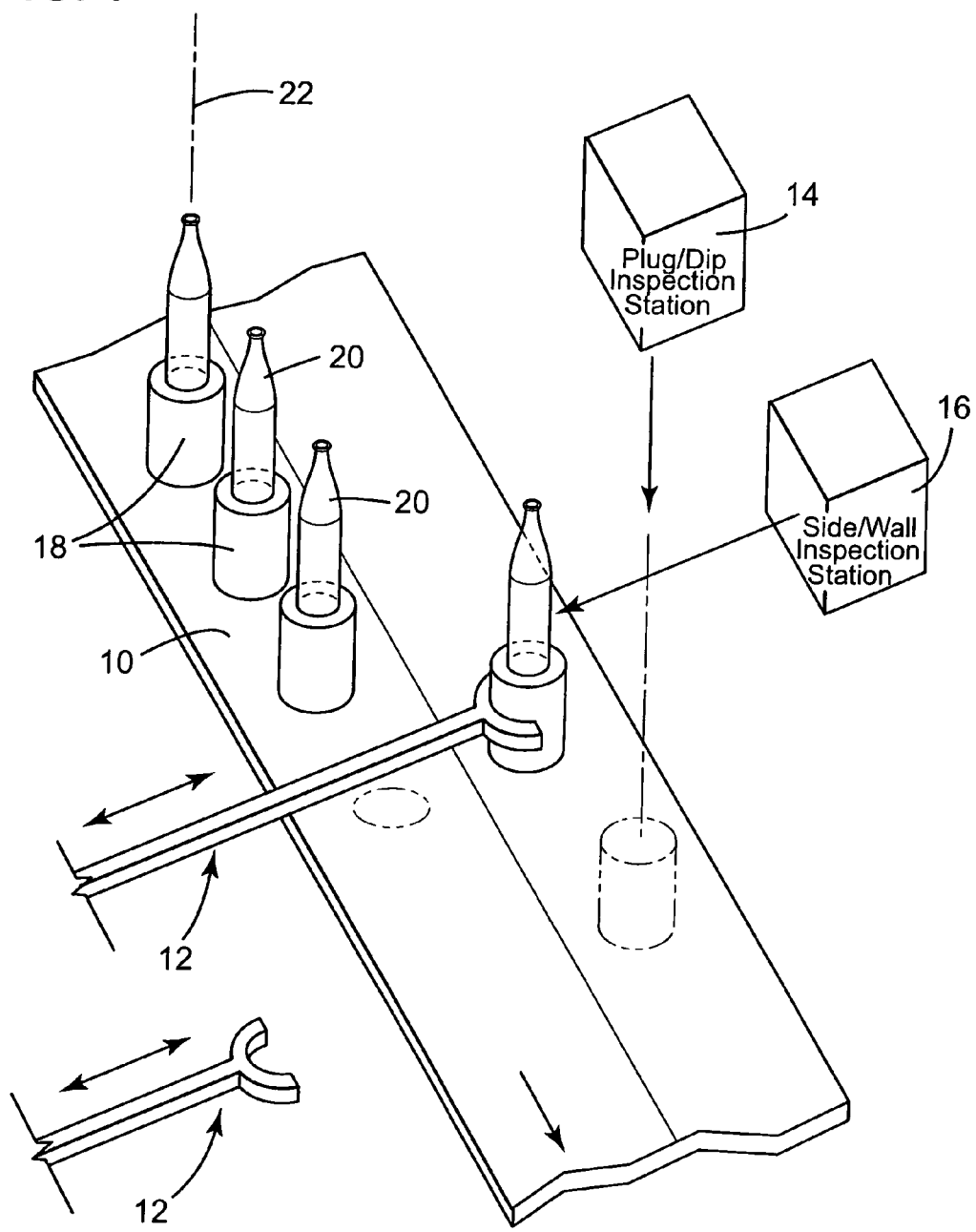
FIG. 1 is an oblique schematic view of an inspection machine having a conveyor which conveys bottles to a series of inspection stations.

An inspection machine is schematically illustrated in FIG. 1. A conveyor system, which is made up of a conveyor 10 and bottle pushing elements (robotic pushers) 12 locate bottles which could be any color and shape, at a number of inspection stations. The invention is not limited to pushers. These devices could be any handling structure that is normally used to control the displacement of a bottle to be tested. Representative inspection stations are shown as a Plug/Dip Inspection Station 14, which would evaluate the dimension (diameter) of the inner and outer cylindrical surfaces of the bottle finish, and a Side Wall Inspection Station 16, which would evaluate the sidewall dimensions of a bottle.

Figure 2:
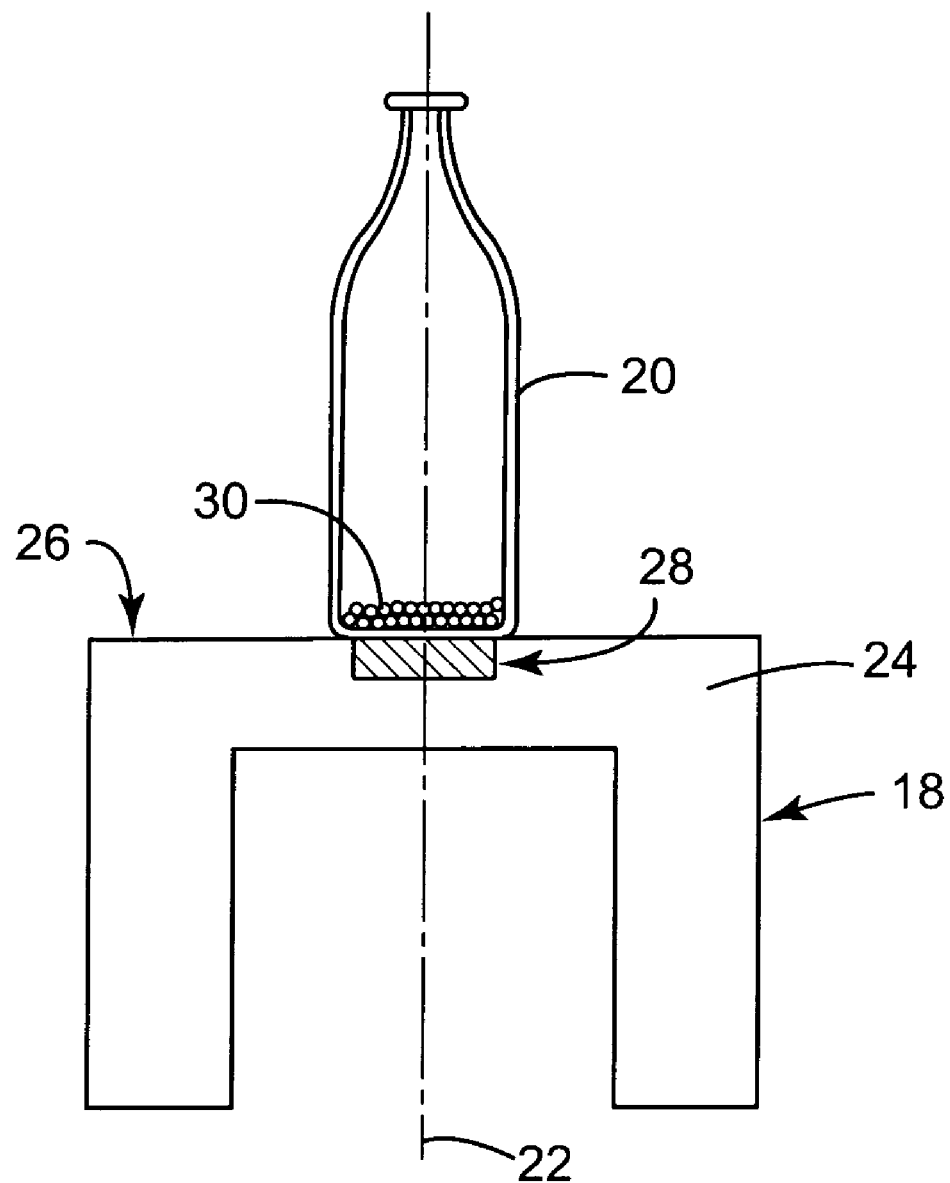
FIG. 2 is an enlarged elevational cross sectional view of a bottle to be inspected supported by an adapter.

In the present application, bottles are replaced by a bottle assembly, which includes a container like adapter 18 and a bottle 20 to be inspected. The container like adaptor 18 has a configuration, which makes it possible for the robotic pusher 12 to handle the container like adaptor 18 in the same manner as a conventionally inspected bottle of the same size. The axis 22 of the container like adaptor is the axis of an equivalent bottle. The container like adaptor 18 (FIG. 2) has a top portion 24 which has a flat top surface 26 for supporting a bottle 20 to be inspected. A centering magnet 28 is mounted in the top portion of the container like adapter 18. The centering magnet has a localized centering effect whereby ferrous objects placed within the field will be aligned closely to a vertical centerline, which coincides with the vertical centerline 22 of the container like adaptor 18. Metallic material 30 (ferrous objects or spheres as shown) are placed in the bottle 20 to be inspected and the bottle 20 is placed centrally onto the centering magnet portion of the top surface of the container like adaptor 18. The attraction between the centering magnet 28 and the metallic spheres 30 holds the bottle 20 on the top surface of the container like adaptor 18 and relocates the axis of the bottle 20 to be inspected to the vertical centerline of the centering magnet and holds the bottle with such coincidence. The particulate size and amount of metallic material can be defined to achieve the desired result. The magnet could be a single magnet or a number of magnets arranged to provide the desired centering effect (four flat rectangular magnets could be used). For purposes of clarity "bottle" has been used to describe the item to be inspected and "container" has been used to define the adaptor. In the glass forming art, these words are often used interchangeably.

The invention claimed is:

1. An apparatus for facilitating the inspection of containers by a machine for inspecting containers, the machine having an inspection station including an inspection device for carrying out an inspection on a container having a vertical axis, relative to a vertical inspection axis, the machine also having a container conveyor system including structure for engaging the side wall of a container and for displacing it to the inspection station where its axis is coincident with the inspection axis, the apparatus for facilitating the inspection comprising:

a container adaptor having a vertical axis and configured for handling by the conveyor system structure so that when said container like adaptor is engaged by the conveyor system structure, the conveyor system structure will deliver said container adaptor to the inspection station with the vertical axis of the container adaptor coincident with the vertical inspection axis, said container adaptor having a horizontal top surface, at least one magnet mounted in or under said top surface having a centering axis coincident with the vertical axis of said container adaptor, a metallic material for placement in the bottom portion of a container so that when a container with said metallic material inside is located on said horizontal top of said container adaptor the at least one magnet will operate on the metallic material to locate the axis of the coincident with the centering axis of the at least one magnet.

2. An object to be inspected according to claim 1, wherein said metallic material comprises ferrous spheres.

3. An apparatus as defined in claim 1, wherein said container adapter has a cylindrical outer configuration.

4. An apparatus as defined in claim 1, wherein said at least one magnet is centrally located in and under said horizontal top surface of said container adapter.

5. An apparatus as defined in claim 1, wherein said at least one magnet comprises a plurality of magnets that are arranged in and under said horizontal top surface of said container adapter to provide the desired centering effect.

6. An apparatus as defined in claim 1, wherein said container adapter is configured to be equivalent to a container having a larger diameter than the diameter of a container to be inspected.

7. A method for facilitating the inspection of containers by a machine for inspecting containers, the machine having an inspection station including an inspection device for carrying out an inspection on a container having a vertical axis, relative to a vertical inspection axis, the machine also having a container conveyor system including a structure for engaging the side wall of a container and for displacing it to the inspection station wherein its axis is effectively coincident with the inspection axis, the method comprising:

provide a container adapter having a vertical axis and configured for handling by the conveyor system structure so that, when the container adapter is engaged by the conveyor system structure, the conveyor system structure will deliver said container adapter to the inspection station with the vertical axis of the container adapter coincident with the vertical inspection axis, said container adapter having a horizontal top surface;

mounting magnet means in or under said horizontal top surface of said container adapter, said magnet means having a centering axis coincident with said vertical axis of said container adapter;

placing magnetically attractable means inside a container at a bottom portion thereof; and placing the container with said magnetically attractable means inside on top of said container adapter above said magnet means, whereupon said magnet means will operate on said magnetically attractable means to cause said axis of the container to be located coincident with said centering axis of said magnet means.

* * * * *